United States Patent [19]

Pacheco et al.

[11] Patent Number: 5,489,703
[45] Date of Patent: Feb. 6, 1996

[54] REACTION EXTRACTION OF ALKYL CARBONATE

[75] Inventors: Michael A. Pacheco, Naperville, Ill.; Franklin D. Darrington, Munster, Ind.; Joann C. Reier, Aurora; Bruce D. Alexander, Villa Park, both of Ill.

[73] Assignee: Amoco Corporation, Chicago, Ill.

[21] Appl. No.: 444,783

[22] Filed: May 19, 1995

[51] Int. Cl.$^6$ .................................................. C07C 68/06
[52] U.S. Cl. ............................................................ 558/277
[58] Field of Search ............................................. 558/277

[56] References Cited

U.S. PATENT DOCUMENTS

| | | | |
|---|---|---|---|
| 3,642,858 | 2/1972 | Frevel et al. | 558/277 |
| 4,661,609 | 4/1987 | Knifton | 558/277 |
| 4,691,041 | 9/1987 | Duranleau et al. | 558/277 |
| 4,734,518 | 3/1988 | Knifton | 558/277 |
| 5,231,212 | 7/1993 | Buysch et al. | 558/277 |

Primary Examiner—Johann Richter
Assistant Examiner—Michael G. Ambrose
Attorney, Agent, or Firm—Thomas A. Yassen; Richard A. Kretchmer

[57] ABSTRACT

An extraction reaction process is provided for reacting feedstocks comprising alkylene carbonate and alkanol to form reaction products comprising alkyl carbonate. The process comprises reacting the feedstocks comprising alkylene carbonate and alkanol in a reaction zone at reaction conditions for producing the reaction products comprising alkyl carbonate. The feedstocks comprising alkylene carbonate and alkanol and the reaction products comprising alkyl carbonate are, substantially concurrently with the reacting step and within the reaction zone, contacted with a selective solvent selective for extracting alkyl carbonate from the reaction zone. The selective solvent comprises a distribution coefficient with respect to the alkyl carbonate that is substantially different than the distribution coefficient of the selective solvent with respect to the alkanol.

20 Claims, 3 Drawing Sheets

REACTION EXTRACTION OF ALKYL CARBONATE

BACKGROUND OF THE INVENTION

This invention relates to a low cost process for producing alkyl carbonate, a potential high oxygen-content gasoline blending component (Oxygenate). More particularly, this invention relates to a process for reacting alkylene carbonate with alkanol to form alkyl carbonate and substantially concurrently extracting such alkyl carbonate with a selective solvent to produce alkyl carbonate in excess of its reaction equilibrium yield.

Oxygenates have been a part of the United States gasoline strategy since the late 1970s. With the Clean Air Act Amendments of 1990 and the government mandate for reformulated gasoline (RFG), the demand for oxygenates has increased even further. The most commonly used oxygenates today am methanol, ethanol, and methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and high cost have dampened industry enthusiasm for these components. As a result of the above, MTBE and homologues of MTBE such as ethyl tertiary butyl ether (ETBE) and methyl tertiary amyl ether (TAME) are often preferred by refiners.

Ether production capacity, however, is limited by ether plant capacity and feedstock availability. MTBE and ETBE both generally utilize an isobutylene-containing feedstock while TAME is generally produced from isoamylene. Isobutylene and isoamylene feedstocks are generally supplied from fluid catalytic cracking units (FCC), fluidized or delayed cokers, or from downstream paraffin isomerization and dehydrogenation facilities. The availability of hydrocarbons having 4 and 5 carbon atoms, the mix of paraffins and olefins, as well as the proportions of iso- and normal olefins are all severely constrained by factors such as crude properties, FCC catalyst properties, FCC operating conditions, coking conditions as well as other refinery operating parameters and variables.

Thus, there exists a great need in the petroleum industry for a low cost method for increasing oxygenate supply that overcomes, avoids, or manages the obstacles described above.

The use of alkyl carbonates, and particularly the dialkyl carbonates in fuels and for commercial chemical applications has been the subject of several patents and patent applications.

For example, European Patent Application Numbers 0 082 688 to Bretherick and 0 098 691 to Spencer disclose the use of dialkyl carbonate and dimethyl carbonate in fuels for use with spark ignition engines.

U.S. Pat. No. 4,380,455 to Smith discloses the use of dialkyl carbonates for preventing the phase separation of hydrous ethanol from liquid hydrocarbon fuel mixtures.

U.S. Pat. No. 4,891,049 to Dillon discloses the use of non-aromatic, metals-free carbonates for reducing particulate emissions from distillate-based fuels such as diesel fuel and jet fuel.

Alkyl carbonates are produced using any of several processes known in the art, each process having attendant advantages and associated penalties. Such processes include phosgene alcoholysis, urea alcoholysis, the carbonylation of alcohols, and alkylene carbonate alcoholysis among others.

One of the oldest methods for manufacturing carbonates employs phosgene. The phosgene is generally contacted with methanol to form methyl chloroformate and thereafter, dimethyl carbonate in accordance with the following reactions:

$$COCl_2 + CH_3OH \rightarrow CH_3OCOCl + HCl$$

$$CH_3OCOCl + CH_3OH \rightarrow CH_3OCOOCH_3 + HCl$$

An associated penalty with the process described above is that it requires the use of toxic phosgene and further leads to the coproduction of other chloride-containing by-products such as alkyl chlorides, which are often toxic themselves. Chlorine-containing by-products such as hydrogen chloride can also be particularly corrosive. Neutralization methods to balance the acidity of these chlorided components, such as the addition of sodium hydroxide (i.e., to facilitate the reaction by the production of sodium chloride and water), can be costly as well as compromise product quality.

Urea alcoholysis can also be employed to produce alkyl carbonates such as dimethyl carbonate. The first alcoholysis step reacts urea with methanol to produce methyl carbamate. The methyl carbamate formed by the first alcoholysis step subsequently reacts with additional methanol to produce dimethyl carbonate. These reactions are typified as follows:

$$C(NH_2)_2O + CH_3OH \xrightarrow{\text{Catalyst}} C(NH_2)(OCH_3)O + NH_3$$

$$C(NH_2)(OCH_3)O + CH_3OH \xrightarrow{\text{Catalyst}} C(OCH_3)_2O + NH_3$$

While the first alcoholysis step to methyl carbamate is thermodynamically favored, the second alcoholysis step to dimethyl carbonate is not and the alkyl carbonate yields attendant to urea alcoholysis are particularly low. As a result, urea alcoholysis processes are not common commercially.

Alkyl carbonates have also been produced through oxidative carbonylation. It is generally known that alkyl carbonates can be produced from alkanol and carbon monoxide in the presence of certain metal chlorides or metal alkoxy chlorides through an oxidation-reduction reaction. An example of such a reaction with methanol and carbon monoxide over a copper chloride catalyst is as follows:

Oxidation:
$$2CH_3OH + 1/2 O_2 + 2CuCl \longrightarrow 2Cu(OCH_3)(Cl) + H_2O$$

Reduction:
$$2Cu(OCH_3)(Cl) + CO \longrightarrow 2CuCl + CH_3O(CO)CH_3$$

Overall:
$$2CH3OH + CO + 1/2 O2 \xrightarrow{\text{CuCl}} (CH_3O)_2CO + H_2O$$

U.S. Pat. No. 4,218,391 to Romano et al. discloses such a process for the production of carbonates comprising reacting an alkanol with oxygen and carbon monoxide in the presence of a catalyst consisting of a copper metal salt of the group of cuprous and cupric salts having a single inorganic anion.

U.S. Pat. No. 5,004,827 to Curnutt discloses a similar process for the production of carbonates comprising contacting an alkanol with carbon monoxide and oxygen in the presence of a heterogeneous catalyst comprising a metal halide such as cupric chloride and/or potassium chloride impregnated on an appropriate support such as activated carbon.

The oxidative carbonylation reaction cannot generally be operated to high conversion because high concentrations of water in the reactor lead to low selectivity and result in undesirably high yields of carbon dioxide. Additionally, excess water can lead to the formation of a variety of copper hydroxy chloride phases of the formula $Cu(Cl)_x(OH)_y \cdot nH_2O$, none of which are particularly effective for the production of carbonates. These oxidative carbonylation reactions are typically conducted at low conversion per reactor pass with an effective strategy for feed/product separation and recycle of the unconverted feed.

Perhaps one of the most promising processes for the production of alkyl carbonates is alkylene carbonate alcoholysis where an alkylene carbonate such as ethylene carbonate is converted to dimethyl carbonate and ethylene glycol through a transesterification step as follows:

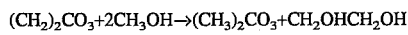

The process is generally conducted in the liquid phase with either a homogeneous or heterogeneous catalyst and provides a single liquid phase product.

Alkylene carbonate alcoholysis has also been the subject of several U.S. patents.

For example, U.S. Pat. No. 3,642,858 to Frevel discloses a process for manufacturing alkyl carbonates which comprises reacting an alkylene carbonate with a non-tertiary hydroxy-containing compound having the formula R—OH in the presence of a catalytic amount of an alkali metal.

U.S. Pat. No. 4,734,518 to Knifton discloses a catalyst and process for producing ethylene glycol and dimethyl carbonate which comprises reacting ethylene carbonate and methanol over a catalyst consisting of bivalent sulfur or bivalent selenium compounds.

U.S. Pat. No. 4,691,041 to Duranleau et al. discloses a catalyst and process for producing ethylene glycol and dimethyl carbonate which comprises reacting ethylene carbonate and methanol over a catalyst consisting of ion exchange resins with quaternary ammonium, sulfonic acid, or carboxylic acid functional groups, alkali and alkaline earth silicates impregnated into silica, or ammonium exchanged zeolites.

U.S. Pat. No. 4,661,609 to Knifton discloses a catalyst and process for producing ethylene glycol and dimethyl carbonate which comprises reacting ethylene carbonate and methanol over a catalyst consisting of zirconium, titanium, or tin.

Canadian Patent No. 2,077,196 to Buysch et al. discloses a process for the continuous transesterification of ethylene carbonate with alcohol in the presence of a catalyst. The transesterification reactants are generally processed countercurrently in a column. The catalyst can be arranged as a fixed bed in the column or can be metered into the column in solution or in suspension with the ethylene carbonate.

Unfortunately, the transesterification reaction of alkylene carbonate is not thermodynamically favored. For example, a transesterification reaction conducted with a feedstock consisting of methanol and ethylene carbonate at a 4/1 molar ratio, a reaction temperature of 100° C., and a reaction pressure of 100 psig, equilibrates to the following approximate product composition:

| Product | Weight Percent |
|---|---|
| Dimethyl Carbonate | 24 |
| Ethylene Glycol | 17 |
| Ethylene Carbonate | 17 |
| Methanol | 42 |

This corresponds to only about 58 percent ethylene carbonate conversion and about 30 percent methanol conversion at equilibrium.

Methods have been suggested to improve the low yield of dimethyl carbonate produced from alkylene carbonate alcoholysis.

For example, U.S. Pat. No. 4,062,884 to Romano et al. discloses a process for preparing dialkyl carbonate by reacting an alcohol with a cyclic carbonate in the presence of a tertiary aliphatic amine while continuously distilling the alcohol/dialkyl carbonate azeotrope from the mixture of reaction products and feed. Distilling and removing fractions of the reaction products drives the transesterification reaction toward higher yields of dialkyl carbonate.

U.S. Pat. No. 3,803,201 to Gilpin et al. discloses a similar process for producing increased yields of dimethyl carbonate. The process comprises reacting alkylene carbonate with a substantial excess of methanol at the boiling point of the reaction mixture and in the presence of a catalyst. During the reaction, an azeotrope of dimethyl carbonate and methanol is removed intermittently or continuously by distillation to increase the yield of dimethyl carbonate.

While such process enhancements are an improvement in some respects, it has been found that distillation steps necessitate the presence of a large recycle stream of unconverted methanol and thereby require excessively large and costly reaction and dimethyl carbonate from methanol distillation equipment. Moreover, the inherent separation inefficiencies attendant to azeotropic distillation methods such as those required to separate the fraction of dimethyl carbonate and methanol that is distilled from the reaction products, combined with their excessive energy costs, compromise the economies of such an investment.

It has now been found that alkylene carbonate alcoholysis process performance can be substantially enhanced in terms of alkylene carbonate and alkanol conversion and alkyl carbonate from the reaction step recovery by reacting alkylene carbonate with alkanol to form alkyl carbonate and concurrently extracting such alkyl carbonate from the reaction step with a selective solvent. This reaction extraction process results in the production of alkyl carbonate in excess of its reaction equilibrium yield.

For purposes of the present invention, alkylene carbonate conversion, alkanol conversion, and alkyl carbonate yield shall be calculated according to the following formulae:

$$\text{Alkylene Carbonate Conv.} = \frac{[\text{Wt Alkylene Carbonate in} - \text{Wt Alkylene Carbonate out}] \times 100}{[\text{Wt Alkylene Carbonate in}]}$$

$$\text{Alkanol Conv.} = \frac{[\text{Wt Alkanol in} - \text{Wt Alkanol out}] \times 100}{[\text{Wt Alkanol in}]}$$

$$\text{Alkyl Carbonate Yield} = \frac{[\text{Wt Alkyl Carbonate out}] \times 100}{[\text{Wt Alkylene Carbonate in}]}$$

It has also been found that concurrently extracting alkyl carbonate with a selective solvent during the reaction step enhances alkylene carbonate alcoholysis process performance without creating or necessitating large alkanol recycle volumes inherent to recovery processes utilizing distillation-based yield enhancement. This finding greatly reduces the capital and operating costs attendant to erecting and operating an alkylene carbonate alcoholysis process.

It has also been found that concurrently extracting alkyl carbonate with a selective solvent during the reaction step enhances alkylene carbonate alcoholysis process performance by not creating and removing an alkyl carbonate/alkanol azeotrope, commonly produced from the reaction products of distillation-based processes, thereby eliminating the need for downstream azeotropic separation steps.

It has also been found that the process of the present invention can be easily enhanced through the addition of a water cosolvent to the stripper section of a liquid-liquid reaction extraction column. Addition of water to the stripper section results in even higher levels of alkylene carbonate conversion and further reduces, through extraction, the amount of alkanol that is undesirably removed from the reaction system with the extract.

For a general understanding of extraction processes, R. W. Cusack; P. Fremeaux; and D. Glatz, A Fresh Look at Liquid-Liquid Extraction, Chemical Engineering, February 1991, discloses the generic use of liquid-liquid extraction and liquid-liquid reaction extraction processes and in particular, uses for such processes such as for the recovery of copper from copper-etching operations.

In addition, U.S. Pat. Nos. 5,328,615 and 5,338,878 to Pacheco et al. disclose processes for extracting alkyl carbonates from feedstocks comprising alkyl carbonate and alkanol using a hydrocarbon selective for extracting alkyl carbonate relative to alkanol. These processes provide a general understanding of liquid-liquid extraction but are not directed to the formation of alkyl carbonate, alkylene carbonate alcoholysis, or reaction extraction.

It is therefore an object of the present invention to provide an effective and efficient process for the production of alkyl carbonate.

It is another object of the present invention to provide a process for the production of alkyl carbonate that can achieve alkylene carbonate and alkanol conversions and alkyl carbonate recovery levels exceeding alkylene carbonate alcoholysis equilibrium.

It is still another object of the present invention to provide a process for the production of alkyl carbonate that achieves enhanced alkylene carbonate and alkanol conversions and alkyl carbonate recovery levels without necessitating large alkanol recycle volumes such as those inherent to enhanced recovery processes utilizing distillation.

It is yet another object of the present invention to provide a process for the production of alkyl carbonate that achieves enhanced alkylene carbonate alcoholysis process performance without removing an alkyl carbonate/alkanol azeotrope from the reaction products as is commonly done with distillation-based processes, thereby eliminating the need to subsequently separate this azeotrope.

Other objects appear herein.

SUMMARY OF THE INVENTION

The above objects can be achieved by providing an extraction reaction process for reacting feedstocks comprising alkylene carbonate and alkanol to form reaction products comprising alkyl carbonate. The process comprises reacting the feedstocks comprising alkylene carbonate and alkanol in a reaction zone at reaction conditions for producing reaction products comprising alkyl carbonate. The feedstocks comprising alkylene carbonate and alkanol and the reaction products comprising alkyl carbonate are, substantially concurrently with the reacting step and within the reaction zone, contacted with a selective solvent selective for extracting alkyl carbonate from the reaction zone. The selective solvent comprises a distribution coefficient with respect to the alkyl carbonate that is substantially different than the distribution coefficient of the selective solvent with respect to the alkanol.

The process in accordance with the present invention can achieve alkylene carbonate conversions of greater than 70 and even 90 percent which is a remarkable improvement over the processes of the prior art which are limited by reaction equilibrium to alkylene carbonate conversion levels of as low as or lower than 60 percent.

The process in accordance with the present invention can also achieve alkanol conversions of greater than 50 and even 75 percent which again is a substantial improvement over the processes of the prior art which are limited by reaction equilibrium to alkanol conversion levels of as low as or lower than 30 percent.

The process of the present invention achieves overall yields of alkyl carbonate in excess of 40 and even 55 percent, which again is a marked improvement over the processes of the prior art which are limited by reaction equilibrium to alkyl carbonate yields of lower than 30 percent.

The process of the present invention achieves these superior levels of yield and conversion performance without necessitating large alkanol recycle volumes inherent to recovery processes utilizing distillation-based yield enhancement. Furthermore, the process of the present invention does not separate and remove an alkyl carbonate/alkanol azeotrope generally removed from the reaction products in distillation-based processes. These azeotropes, created in distillation-based processes, are particularly difficult and costly to separate. These aspects of the present invention greatly reduce the capital and operating costs attendant to erecting an alkylene alcoholysis process.

Where the reaction is conducted in a reaction extraction column, the process of the present invention can be easily enhanced through the addition of a water cosolvent to the stripper section of such column. Addition of water to the bottom of the stripper section results in a process that not only produces alkyl carbonate yields in excess of equilibrium but substantially converts any trace amounts of alkylene carbonate, that would otherwise escape to the raffinate product, to alkylene glycol, further improving alkylene carbonate conversion. Moreover, the enhanced process also reduces, through extraction, the amount of alkanol that is undesirably removed with the extract.

BRIEF DESCRIPTION OF THE INVENTION

Figure 1:
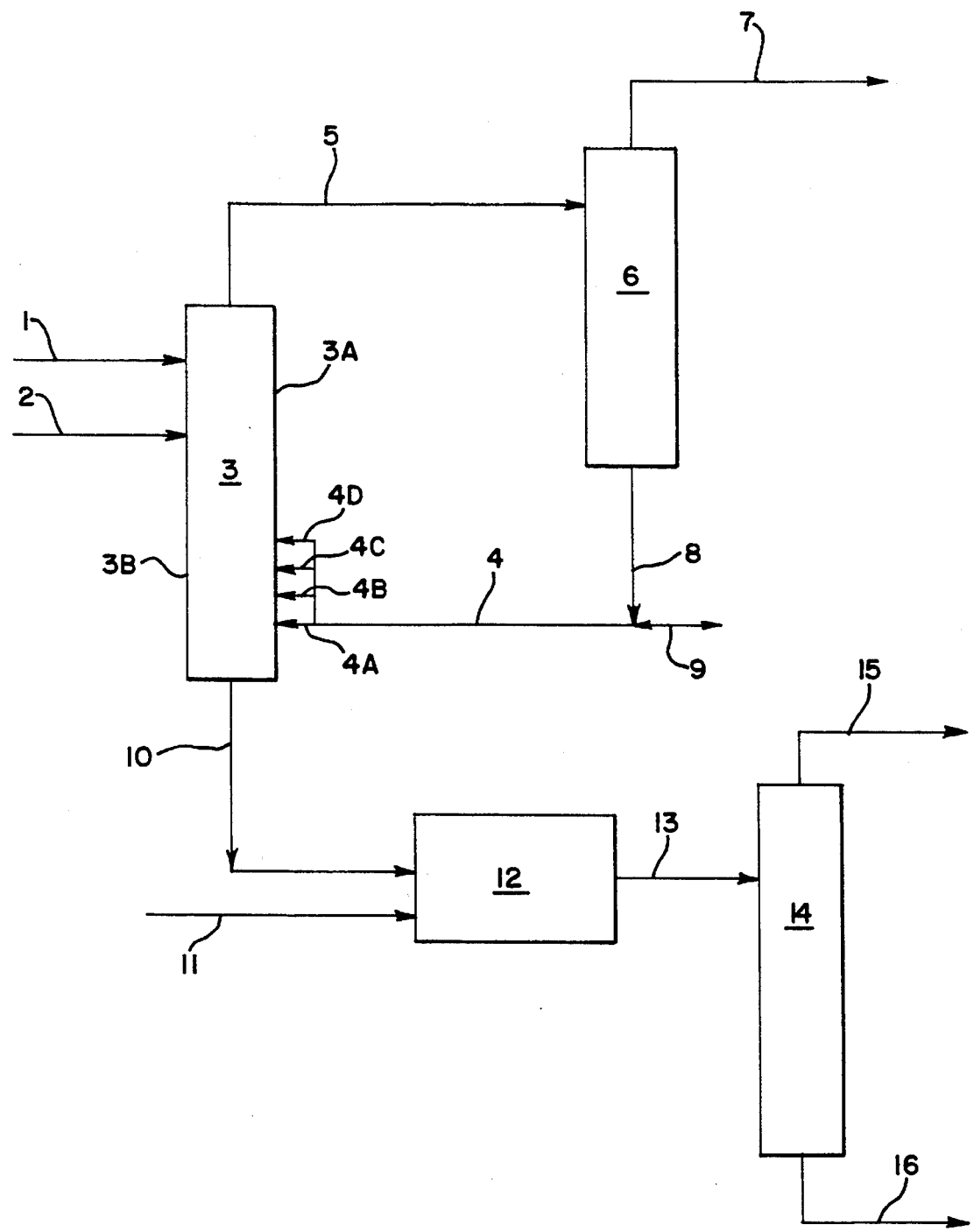
FIG. 1 is an extraction reaction process flow diagram for the manufacture of alkyl carbonate in accordance with the process of the present invention.

The feedstock or feedstocks suitable for use with the process of the present invention comprise at least one alkanol and at least one alkylene carbonate. The feedstock(s), when composited, generally comprise alkanol and alkylene carbonate at a molar ratio of from about 2:1 to about 8:1, preferably from about 2:1 to about 5:1, and more preferably from about 2:1 to about 3:1 for best results. Composited alkanol and alkylene carbonate feedstock ranges outside of the above-described ranges can result in lower alkyl carbonate yield through either insufficient stoichiometric alkanol or excessively high alkanol amounts resulting in increased reaction space velocity and additional alkanol recovery costs.

Alkylene carbonate components suitable for use with the process of the present invention generally comport with the following formula:

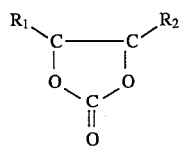
(1)

wherein $R_1$ and $R_2$ can be the same or different of either hydrogen, alkyl having less than 8 and preferably less than 5 carbon atoms, or aryl having from 6 to 9 and preferably from 6 to 8 carbon atoms.

Alkylene carbonate can be formed through any of several ways known in the art, one of which includes the catalytic derivation of alkylene carbonate from epoxides and carbon dioxide as follows:

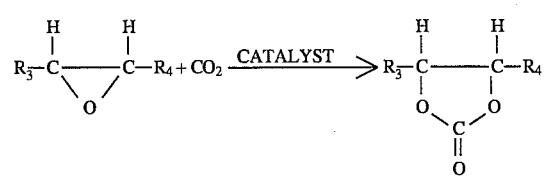
(2)

wherein $R_3$ and $R_4$ can be the same or different of either hydrogen, alkyl having less than 8 and preferably less than 5 carbon atoms, or aryl having from 6 to 9 and preferably from 6 to 8 carbon atoms. Suitable catalysts for the formation of alkylene carbonate from epoxides and carbon dioxide include inorganic bases such as sodium hydroxide and sodium carbonate and organic nitrogen bases such as tertiary amines, quarternary ammonium bases, and salts of these nitrogen bases such as their carbonates and halides. Particularly, preferred catalysts are the quaternary ammonium halides. The reaction of alkylene carbonate and carbon dioxide over a catalyst comprising quaternary ammonium halide is particularly rapid and highly exothermic. Average reaction temperatures generally range from about 200° F. to about 500° F., preferably from about 212° F. to about 482° F., and more preferably from about 300° F. to about 400° F. for best results. Suitable reaction pressures generally range from about 140 psig to about 4400 psig and preferably from about 730 psig to about 2200 psig for best results.

Epoxides useful for producing alkylene carbonate can be formed by one or more of several methods including, but not limited to, the catalytic oxidation of alkylenes. Such a reaction for the formation of ethylene oxide from ethylene, catalyzed by a silver catalyst and at a reaction temperature of 482° F., is as follows:

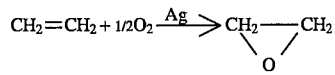
(3)

Suitable epoxides may also be formed via the chlorohydrin route. For example, propylene oxide can be formed by reacting propylene sequentially with chlorine and concentrated aqueous hydroxide as follows:

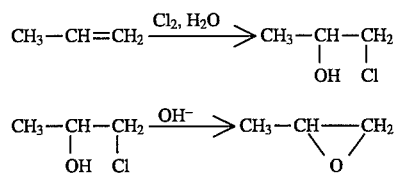
(4)

Suitable epoxides may also be produced through peroxidation. For example, propylene oxide has been commercially produced via peroxidation of isobutane followed by reaction with propylene as follows:

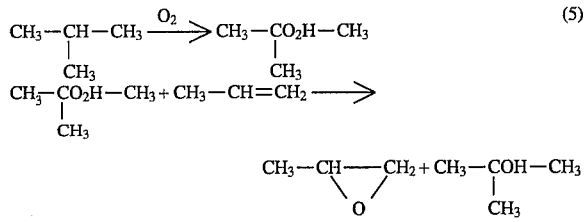
(5)

Alkylene carbonate can also be formed directly from alkylene without formation of an intermediate epoxide. For example, propylene carbonate can be formed directly from propylene, carbon dioxide, and water in the presence of thallic oxide or a weak thallic salt as follows:

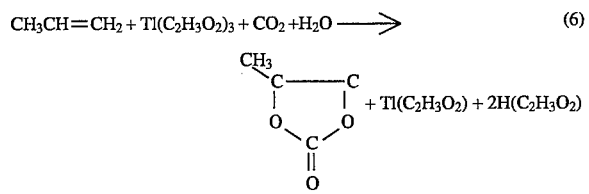
(6)

The reaction can generally be carded out at any convenient temperature but is preferably conducted at temperatures ranging from about room temperature up to the decomposition temperature of thallic compounds which commonly occurs at about 250° F. In order to achieve more desirable reaction rates, the reaction temperatures preferably range from about 100° F. to about 212° F. and more preferably from about 120° F. to about 180° F. for best results. The reaction pressure generally ranges from about atmospheric pressure to about 6000 psig and preferably from about 800 psig to about 1500 psig for best results.

Suitable alkanol components generally include monohydroxy aliphatic and aryl alkanols having from 1 to 9 carbon atoms, preferably monohydroxy aliphatic alcohols having from 1 to 4 carbon atoms and aryl alcohols having 6 carbon atoms, and more preferably monohydroxy aliphatic alcohols having from 1 to 3 carbon atoms and aryl alcohols having 6 carbon atoms for best results. Generally, the alkanol in the feedstock will correspond to the alkyl radical of the desired alkyl carbonate. For example, where dimethyl carbonate is the desired alkyl carbonate, methanol is a preferred alkanol. Correspondingly, where diethyl carbonate is the alkyl carbonate, ethanol is a preferred alkanol.

The cost of the particular alkanol selected can also be decisive as to which alkyl carbonate is produced in accordance with the present invention. External factors such as ethanol subsidies generally can and often do affect the economic balance between the selection of ethanol and methanol. Additionally, the demand for methanol and ethanol for ether manufacture may also indirectly affect the raw material costs of alkanol feedstocks necessary for the production of alkyl carbonates.

While any of the above-described alkylene carbonates and alkanols are suitable for use with the process of the present invention, it is recognized that an end use for the separated alkyl carbonate product can be as a gasoline blending component. Where gasoline is the end product to which the alkyl carbonate is blended, it is preferred that the alkylene carbonate and alkanol be selected such that the alkyl carbonate produced boils substantially within the temperature range of from about 50° F. to about 450° F. at atmospheric pressure for best results. Alkyl carbonate components having more than 6 carbon atoms are not generally blended to gasoline since their endpoint temperature can often exceed the end point temperature specification of many gasolines. Where petroleum distillates such as furnace oil and diesel fuel are the end products to which the alkyl carbonate is blended, it is preferred that the alkylene carbonate and alkanol be selected such that their reaction product alkyl carbonate boils within a temperature range of from about 250° F. to about 700° F. at atmospheric pressure for best results.

Once the alkylene carbonate has been produced, it is generally reacted with alkanol through a transesterification reaction in the presence or absence of a catalyst, to produce alkyl carbonate and glycol. For example, ethylene carbonate can be reacted with methanol to form dimethyl carbonate and ethylene glycol as follows:

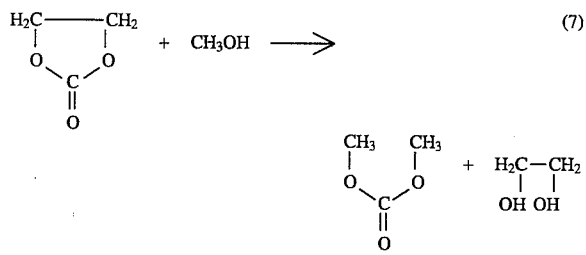
(7)

Similarly, propylene carbonate can be reacted with methanol to form dimethyl carbonate and propylene glycol as follows:

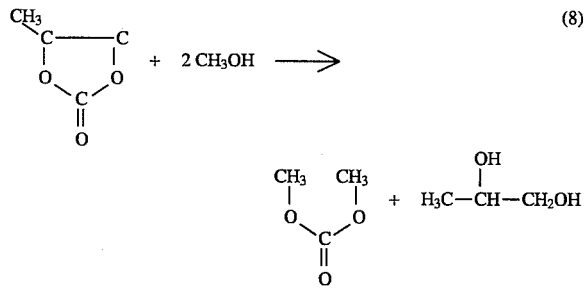
(8)

These reaction steps for converting alkylene carbonate and alkanol to alkyl carbonate and alkylene glycol generally occur as two sequential steps. Addition of the first molecule of methanol to the alkylene carbonate generally results in the production of a hydroxy-alkyl methyl carbonate. Addition of the second molecule of methanol results in the production of dimethyl carbonate and alkylene glycol. The intermediate hydroxy-alkyl methyl carbonate generally builds to a maximum concentration faster than the equilibrium dimethyl carbonate concentration is reached.

The transesterification reaction can be enhanced through use of suitable liquid or solid catalytic materials. Suitable catalysts include the alkyl or aryl ammonium salts, where the anion can be a halide, carbonate, bicarbonate, hydroxide, alkoxide, dihydroxy phosphate, or bisulfate and solid acid or solid base catalysts such as, but not limited to, sulfated polystyrene resins and zeolitic molecular sieves. The preferred catalysts generally comprise the alkali metal carbonates, alkali metal hydroxides, and the sulfated polystyrene resins, and, in particular, potassium carbonate.

The catalyst can be utilized as a solid, as a solubilized solid, or in liquid form with the preferred form being that of a solubilized solid. A solid catalyst such as potassium carbonate can be solubilized in one or more of the alkylene carbonate stream, alkanol stream, selective solvent stream, or another stream that may be conveyed to the reaction vessel. A solid catalyst may also be employed in a fixed bed or ebullated bed arrangement or may be fluidized in a manner so as to enhance the transesterification reaction.

Transesterification reaction conditions generally comprise a reaction temperature ranging from about 32° F. to about 500° F., preferably from about 70° F. to about 400° F., and more preferably from about 100° F. to about 300° F. for best results. Excessively high temperatures can result in the decomposition of the alkyl carbonate into undesirable thermolysis products such as carbon dioxide and reduced phase separation in the reaction extraction vessel. Exceedingly low temperatures can result in reduced alkylene carbonate and alkanol conversion. Suitable reaction pressures generally range from about 0 psig to about 5000 psig, preferably from about 50 psig to about 1000 psig, and more preferably from about 50 psig to about 500 psig for best results. Excessively low pressures can result in vaporization of the alkanol resulting in carryover of the alkanol with the alkyl carbonate-containing product.

FIG. 1 is a reaction extraction process flow diagram for the production of alkyl carbonate in accordance with the process of the present invention.

A first feedstock comprising alkylene carbonate and optionally alkanol and/or a solubilized solid catalyst is conveyed through conduit 1 to a liquid-liquid reaction extraction column 3. A second feedstock comprising alkanol and optionally a solubilized solid catalyst and/or alkylene carbonate is conveyed through conduit 2 to liquid-liquid reaction extraction column 3 at a location below first feedstock conduit 1. The liquid-liquid reaction extraction column 3 generally comprises a top rectification section or rectifying section 3A which defines the section of the liquid-liquid reaction extraction column above the lowest primary feedstock inlet conduit 2 and a bottom stripper or stripping section 3B located below the lowest primary feedstock inlet conduit 2 and below the rectifying section 3A.

The liquid-liquid reaction extraction column 3 defines the zone within which the transesterification reaction takes place as well as provides a particular number of theoretical stages of extraction separation. For purposes of the present invention, the term "theoretical stage of separation" shall be defined as a separation step wherein the solvent extracted extract stream and raffinate stream from the reaction extraction step exist in perfect equilibrium with each other at the particular set of process conditions and stage compositions and wherein the facilities exist for separating such streams. The number of theoretical stages of separation may be provided by a substantially larger number of mechanical plates or trays than the projected number of theoretical stages, wherein tray efficiencies are below 100 percent.

A selective solvent, comprising hydrocarbon selective for extracting alkyl carbonates relative to alkanol is added to the liquid-liquid or reaction extraction column 3 through one or more of conduits 4A, 4B, 4C, and 4D. The selective solvent generally proceeds upwardly through the liquid-liquid reaction extraction column 3 and countercurrently with the first and second feedstocks and the reaction products produced therefrom comprising alkyl carbonate and alkylene glycol, so as to preferentially extract the alkyl carbonate.

An overhead stream or extract stream is withdrawn from the top of the liquid-liquid reaction extraction column 3 through conduit 5. The extract stream generally contains a substantial portion of the alkyl carbonate component produced from the transesterification reaction and the selective solvent for extracting alkyl carbonates. The extract stream from conduit 5 is generally directed to a separation vessel 6 or directly to storage wherein the process is once-through solvent reaction extraction. The separation vessel 6 is provided for separating the extract stream into a stream containing a high concentration of the alkyl carbonate component and a stream containing a high concentration of the selective solvent. The separation vessel 6 can be, but is not limited to a single stage flash separator, a distillation column, a stripper column, among other separation devices known to those skilled in the art of chemical separation.

The stream containing a high concentration of alkyl carbonate is conveyed through conduit 7 to any of numerous end uses including, but not limited to, commercial chemical uses or gasoline or distillate blending component storage. The stream containing a high concentration of the selective solvent is generally conveyed through conduit 8 where the stream can be directed to conduit 4 for recycling selective solvent back to selective solvent conduits 4A, 4B, 4C, and/or 4D. Come and go conduit 9 is provided as a supply line to provide additional selective solvent to the liquid-liquid reaction extraction column 3 or to remove excessive amounts of selective solvent from the system.

A bottoms stream or raffinate stream is withdrawn from the bottom of the liquid-liquid reaction extraction column 3 through conduit 10. The raffinate stream generally contains a substantial portion of the alkylene glycol reaction product, unconverted alkanol which is generally provided to the reaction extraction step in excess of stoichiometric requirements, trace amounts of alkyl carbonate, and any unconverted alkylene carbonate feedstock. Where there is incomplete conversion of alkylene carbonate and it is desirable to reduce the impurity levels of alkylene carbonate in the alkylene glycol, the raffinate stream from conduit 10 can be directed to a hydrolysis reactor 12. A water stream from a water conduit 11 is also directed to the hydrolysis reactor 12 where it is reacted with the alkylene carbonate to form alkylene glycol and carbon dioxide and with alkyl carbonate to form alkanol and carbon dioxide. For ethylene carbonate and water, the reaction would appear as follows:

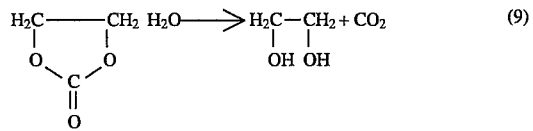

(9)

Suitable hydrolysis catalysts are substantially similar to those described as useful for catalyzing the transesterification reaction. Where sufficient transesterification catalyst remains in solution with the raffinate exiting the liquid-liquid reaction extraction column 3, additional make-up catalyst requirements may be minimal for the additional hydrolysis step. However, some make-up catalyst may be required for the hydrolysis reaction step and can be added in solution with the water from conduit 11 or separately. The hydrolysis reaction conditions of temperature and pressure fall within the ranges set forth hereabove with regard to the transesterification reaction.

The reaction product from the hydrolysis reactor comprising alkylene glycol and carbon dioxide is directed through conduit 13 to a final separation vessel 14. The separation vessel 14 is provided for minimally separating carbon dioxide from the hydrolysis product stream comprising alkylene glycol, alkanol, and carbon dioxide. The separation vessel 14 can be, but is not limited to a single stage flash separator, a distillation column, a stripper column, an extraction column, and a distillation extraction column among other separation devices known to those skilled in the art of chemical separation. The carbon dioxide-containing stream is removed from the separator vessel 14 through conduit 15 while the alkanol and alkylene glycol-containing stream is removed through conduit 16.

Where it is desirable to further separate alkanol from the alkylene glycol, the separation vessel 14 may be followed by a second separation vessel for separating the alkanol from the alkylene glycol. Another alternative that may be considered is to operate the separation vessel 14 to separate alkanol and carbon dioxide from the alkylene glycol followed by a subsequent separation step to remove the carbon dioxide from the separated alkanol and carbon dioxide. It may also be desirable to recycle at least a portion of any alkanol recovered at this point to the reaction extraction column 3. The selection of which separation scheme to employ can be made in consideration of the specific requirements of the operation and using engineering principals known in the art of chemical separation.

The selective solvent generally comprises a hydrocarbon selective for extracting alkyl carbonate relative to alkanol and preferably relative to alkanol, alkylene carbonate, and alkylene glycol. Hydrocarbon selective for extracting alkyl carbonate relative to alkanol will have a "substantially different distribution coefficient" with respect to alkyl carbonate relative to alkanol. For purposes of the present invention, the distribution coefficient for alkyl carbonate shall be calculated as the weight percent of alkyl carbonate in the extract phase divided by the weight percent of alkyl carbonate in the raffinate phase. The distribution coefficient for alkanol shall be calculated as the weight percent of alkanol in the extract phase divided by the weight percent of alkanol in the raffinate phase. Substantially different distribution coefficients with respect to alkyl carbonate relative to alkanol shall mean where the ratio of the alkyl carbonate and alkanol distribution coefficients is greater than 10.0. Selective solvents having low polarity generally provide improved selectivity for extracting alkyl carbonate relative to alkanol.

Suitable hydrocarbon solvents selective for extracting alkyl carbonate relative to alkanol generally have an API gravity ranging from about 10° API to about 100° API, preferably from about 20° API to about 100° API, and more preferably from about 30° API to about 100° API for best results. Hydrocarbon having a gravity within these ranges generally facilitates better mixing and reaction extraction performance wherein suitable recoveries of alkyl carbonate to extract and alkanol to raffinate can be achieved with fewer theoretical stages of separation.

The selective solvent, when added to the reaction extraction step, should combine with the respective feedstocks and reaction products to form two phases or mixtures having substantially different specific gravities. The first mixture or phase generally comprises the alkyl carbonate-extracted product and a large portion of the selective solvent while the second mixture or phase generally comprises the unconverted alkylene carbonate and alkanol, the alkylene glycol product, and a smaller portion of the selective solvent. For purposes of the present invention, "substantially different specific gravities" shall mean extract and raffinate phases where the specific gravity of the phase having the higher specific gravity divided by the specific gravity of the phase having the lower specific gravity is at least 1.10.

Preferably the selective solvent has an aromatics concentration of more than 1 percent by weight, preferably ranging from about 5 percent by weight to about 50 percent by weight, and more preferably from about 10 percent by weight to about 40 percent by weight for best results. It has been found that the aromatics concentration of the selective solvent correlates favorably with the effectiveness of the solvent for extracting alkyl carbonates. However, where aromaticity becomes excessive, the specific gravity can be increased to a level where the small difference in extract and raffinate specific gravities adversely affects solvent extraction performance.

Preferably, the selective solvent has an olefin concentration of less than 80 percent by weight, preferably ranging from about 0 percent by weight to about 40 percent by weight, and more preferably from about 0 percent by weight to about 25 percent by weight for best results. It has also been found that the olefin concentration of the selective solvent correlates inversely with the effectiveness of the solvent for extracting alkyl carbonates.

It has also been found that high proportions of branched paraffinic components can also adversely affect solvent extraction performance. Such components are present in highest concentrations in refinery alkylation and isomerization unit products.

Gasoline boiling range components satisfy many of the selective solvent criteria described above. Suitable selective solvents generally comprise most refinery hydrocarbon streams boiling at a temperature ranging from about 50° F. and about 450° F. at atmospheric pressure. These streams include, but are not limited to, fluid catalytic cracking process naphtha, fluid or delayed coking process naphtha, light virgin naphtha, heavy virgin naphtha, hydrocracker naphtha, hydrotreating process naphthas, alkylate, isomerate, catalytic reformate, and aromatic derivatives of these streams such as benzene, toluene, xylene, and combinations thereof. The catalytic reformate and catalytic cracking process naphthas can often be split into narrower boiling range streams such as light and heavy catalytic naphtha and light and heavy catalytic reformate, which can be specifically customized for use as a solvent in accordance with the present invention. The preferred streams are light virgin naphtha, catalytic cracking naphthas including light and heavy catalytic cracking unit naphtha, catalytic reformate including light and heavy catalytic reformate, and the aromatic derivatives of such refinery hydrocarbon streams including benzene and toluene.

Distillate boiling range hydrocarbon has not been regulated for oxygenate content at this time. Therefore, the need for an inexpensive oxygenate for distillate fuels such as diesel fuel and furnace oil is not as compelling as for gasoline. However, distillates also satisfy many of the selective solvent criteria described above and can also be effective selective solvents. Suitable distillate-containing selective solvents generally comprise refinery hydrocarbon streams boiling at a temperature ranging from about 150° F. to about 700° F. at atmospheric pressure and preferably from about 250° F. to about 700° F. for best results. These streams include, but are not limited to, virgin light middle distillate, virgin heavy middle distillate, fluid catalytic cracking process light catalytic cycle oil, coker still distillate, hydrocracker distillate, and the collective and individually hydrotreated embodiments of these streams. The preferred streams are the collective and individually hydrotreated embodiments of fluid catalytic cracking process light catalytic cycle oil, coker still distillate, and hydrocracker distillate.

It is also anticipated that one or more of the above hydrocarbon streams can be combined for use as a selective solvent. In many cases, reaction extraction performance for the various solvent alternatives may be comparable. In these cases, logistics such as the volume availability of a stream, location of the nearest connection, and short term economics may be determinative as to what solvent is utilized. Therefore, the process of the present invention offers substantial flexibility as to solvent alternatives. A further advantage of the selective solvent of the present invention is that the solvent need not be recovered from the extract stream and can proceed directly to gasoline or distillate blending along with the recovered alkyl carbonate. It is preferred that gasoline and distillate boiling range solvents not be commingled as this may require one or more additional separation steps.

The selective solvent is generally added to the liquid-liquid reaction extraction column at a solvent to feed volume ratio based on the total volume of one hundred percent solvent added (from all locations) per volume of the stoichiometrically limiting component added. In many, and perhaps most cases, the stoichiometrically limiting component will be alkylene carbonate. The selective solvent to feed volume ratio is generally adjusted to provide the desired alkyl carbonate yield and extraction performance and alkylene carbonate conversion level desired. The selective solvent to feed volume ratio for the process of the present invention generally ranges from about 50:1 to about 1:1, commonly from about 30:1 to about 3:1, and often from about 20:1 to about 5:1.

The selective solvent is generally loaded in a manner so as to produce an extract containing from about 1 percent to about 50 percent by weight of alkyl carbonate in the total extract stream, commonly from about 2 percent to about 40 percent by weight, and often from about 3 percent to about 30 percent by weight. The selective solvent loading is, to some extent, a function of the number and type (i.e., rectifying or stripping) of theoretical stages of separation in the reaction extraction column and the solvent to feed volume ratio. Columns with more theoretical stages can achieve greater loadings and hence, can operate at lower solvent to feed volume ratios. Exceeding the loading ranges described above, however, can result in alkyl carbonate losses to the raffinate stream and lower alkylene carbonate conversion levels. Under most configurations, the process of the present invention can achieve low alkyl carbonate loss levels to the raffinate stream of less than 15 percent by weight of the raffinate, commonly less than 2 percent by weight, and often less than 0.1 percent by weight of the raffinate.

Overall, the process in accordance with the present invention generally recovers a substantial portion of the alkyl carbonate product from the reaction zone to the extract stream. For purposes of the present invention, a "substantial portion of alkyl carbonate removed from the reaction zone" shall mean the recovery to extract of at least 80 percent by weight of the alkyl carbonate produced as either extract or raffinate exiting the reaction extraction column. It is not uncommon, however, for alkyl carbonate recoveries to exceed as much as 75 percent by weight and often as much as 90 percent by weight or higher.

It has also been found that a second cosolvent may also be employed to further enhance the effectiveness of the reaction extraction process in accordance with the present invention.

As described previously, the raffinate stream comprising alkylene glycol and unconverted alkanol and alkylene carbonate can be directed to a hydrolysis reactor for converting unconverted alkylene carbonate to alkylene glycol as described above. However, it is also contemplated that this hydrolysis conversion can be achieved, in whole or in part, at the bottom of the reaction extraction column. For example, water can be injected into the stripping section of the reaction extraction column for the purpose of first converting the unconverted alkylene carbonate to alkylene glycol and converting trace amounts of alkyl carbonate to alkanol without requiring the capital investment necessary to achieve this step through external hydrolysis reactors. A secondary benefit is also achieved in that the injection of water provides ancillary extraction of the alkanol from the reaction products causing the extracted alkanol and water to exit the reaction extraction column with the raffinate. In this manner, the extract stream retains lower concentrations of unconverted alkanol and the raffinate stream retains lower concentrations of unconverted alkylene carbonate. However, it is important that the refiner select a location for water injection that does not excessively shift the conversion of alkylene carbonate from alkyl carbonate to alkylene glycol. For this reason, it is anticipated that the preferred water injection point would be in the stripping section in proximity to the bottom of the reaction extraction column.

The liquid-liquid reaction extraction step in accordance with the present invention can be operated using numerous combinations of hardware and process variables, with various feedstock characteristics, and can be customized to meet wide-ranging product requirements. The overall extraction separation efficiency is generally a function of the number of theoretical stages of separation in the reaction extraction column, whether the theoretical stages are rectifying or stripping, the efficiency of the extraction device and internals, and the feedstock characteristics and production specifications required. For example, allocating an excessively high percentage of the theoretical stages to the rectification section can result in unfavorable decreases in alkylene carbonate conversion, alkanol conversion, and alkyl carbonate yield. It has also been found that the particular alkyl radical of the alkyl carbonate can affect the solvent to feed requirements and/or theoretical stages required to synthesize and extract the alkyl carbonate from the reaction extraction column. For example, diethyl carbonate is often more easily extracted from a reaction extraction system than dimethyl carbonate and may require fewer theoretical stripping stages and/or a lower selective solvent to feed volume ratio.

The reaction extraction process in accordance with the present invention generally requires at least one theoretical stage of separation, preferably at least two theoretical stages of separation, and more preferably at least three theoretical stages of separation for best results. It is also preferred that the process have at least two stages of stripping reaction extraction for best results.

The various hardware alternatives for liquid-liquid reaction extraction include, but are not limited to, single and multiple solvent liquid-liquid reaction extraction columns and rotary extraction devices.

A commonly used device, suitable for reaction extraction in accordance with the present invention, is the liquid-liquid reaction extraction column. Liquid-liquid reaction extraction is generally conducted counter-currently wherein the liquid having the lower API gravity (i.e. higher density) is added at a higher location in the reaction extraction column in a manner so that the liquid will initially proceed downwardly, and the liquid having the higher API gravity (i.e. lower density) is added at a lower location in the column in a manner so that the liquid will initially proceed upwardly. The lower API gravity liquid may either be one or more of the feedstocks and/or the reaction products synthesized therefrom or the selective solvent. Most commonly, the reacting feedstocks enter at the top of the reaction extraction column whereby the unreacted feedstocks and reaction products generally proceed downwardly through the reaction extraction column.

Liquid-liquid reaction extraction columns also generally comprise mixing and separation internals for increasing reaction and separation efficiency. These separation internals can include mechanisms such as valve, sieve, or bubble cap trays or packing elements including, but not limited to, pall rings, grid packing, or other mechanisms known in the art of chemical separation. The higher the efficiency of these separation internals, the better the reaction extraction performance.

The liquid-liquid reaction extraction device can also include rotary reaction extraction devices wherein the feedstock and solvent are injected into the center of a rotating cylinder comprising a plurality of holes. The rotating cylinder is encased within a rotating cylinder shell. The cylinder is rotated at an angular velocity sufficient for the higher density component to migrate outside of the cylinder and into the shell wherein it is removed, and the lower density component to migrate towards the center of the rotating cylinder from where it is withdrawn.

Other reaction extraction methods and embodiments are also anticipated for use with the present invention from an understanding of chemical separation methods known in the art.

The liquid-liquid reaction extraction column process conditions can comprise a single reaction extraction temperature ranging from about 32° F. to about 500° F., preferably from about 70° F. to about 400° F., and more preferably from about 100° F. to about 300° F. for best results. It is also contemplated that the refiner may choose to create or modify the temperature profile of the liquid-liquid reaction extraction column to optimize or enhance reaction extraction performance. Reaction pressures generally range from about 0 psig to about 5000 psig, preferably from about 50 psig to about 1000 psig, and more preferably from about 50 psig to about 500 psig for best results.

The extract stream comprising alkyl carbonate and the selective solvent can be directed to a separation step for concentrating alkyl carbonate and recovering the selective solvent for recycling back to the reaction extraction step. An extract stream separation step may not be necessary wherein a suitable and readily available gasoline blending component is utilized as the selective solvent. However, separation of the extract stream can advantageously provide a more homogeneous oxygenate-containing gasoline or distillate blending component which can provide product blending benefits.

The overhead product from the separation step for concentrating the alkyl carbonate will generally contain from about 5 percent by weight to about 100 percent by weight and commonly from about 40 percent by weight to about 80 percent by weight of alkyl carbonate. The balance of the overhead product generally comprises the selective solvent and minor amounts of alkanol (less than 5 percent by weight). Preferably, the overhead stream comprises less than 1 percent by weight alkanol and more preferably less than 0.1 percent by weight for best results.

The bottoms product from such an alkyl carbonate from selective solvent separation step generally comprises the selective solvent and alkanol. This fraction can be recycled back to the reaction extraction step to reduce the amounts of make-up selective solvent and alkanol that must be added to the reaction extraction column to maintain performance. The recycle fraction can be directed to the selective solvent inlet line(s) or can be directed independently to the reaction extraction column in a more optimal location based on the composition of the recycle stream. For example, it is preferred that fresh make-up selective solvent be added closer to the bottom of the reaction extraction column and recycle selective solvent be added at higher locations in the extraction column if the fresh selective solvent contains less alkanol and/or other impurities than the recycle selective solvent.

The process of the present invention provides substantially improved performance over any of the processes or combinations of processes taught in the prior art.

Most notably, the process in accordance with the present invention can achieve alkylene carbonate conversions of greater than 40 percent, commonly greater than 70 percent, and often greater than 90 percent. This is a remarkable improvement over the processes of the prior art which are limited by reaction equilibrium to alkylene carbonate conversion levels of as low as or lower than 60 percent.

The process in accordance with the present invention can also achieve alkanol conversions of greater than 30 percent, commonly greater than 50 percent, and often greater than 75 percent. This also is a remarkable improvement over the processes of the prior art which are limited by reaction equilibrium to alkanol conversion levels of as low as or lower than 30 percent.

Still another beneficial result of the superior alkylene carbonate and methanol conversion levels achieved by the process of the present invention is that superior yields of alkyl carbonate can be achieved in excess of 30 percent, commonly greater than 40 percent, and often greater than 55 percent. This again is a remarkable improvement over the processes of the prior art which are limited by reaction equilibrium to alkyl carbonate yields of lower than 30 percent.

The process of the present invention achieves these superior levels of yield and conversion performance without necessitating large alkanol recycle volumes inherent to recovery processes utilizing distillation-based yield enhancement. Alkanol recycle volumes are substantially reduced due to the separation precision of the extractive aspects of the reaction extraction process which are an enormous step forward from the prior art methods reliant upon distillation. This finding greatly reduces the capital and operating costs attendant to erecting an alkylene alcoholysis process as equipment cost in terms of size and horsepower is greatly reduced and day to day solvent and energy costs are minimized by reducing the volumes of alkanol required to reach the desired level of alkylene carbonate conversion.

The process of the present invention achieves these superior levels of yield and conversion performance without creating and removing an alkyl carbonate/alkanol azeotrope removed from the reaction products in distillation-based processes. These azeotropes, created in distillation-based processes, are particularly difficult and costly to separate.

The process of the present invention can be easily enhanced through the addition of a water cosolvent to the stripper section of the reaction extraction column. Addition of water to the bottom of the stripper section results in a process that not only produces alkyl carbonate yields in excess of equilibrium but substantially converts any trace amounts of alkylene carbonate (or alkyl carbonate), that would otherwise escape to the raffinate product, to alkylene glycol (or alkanol) further improving alkylene carbonate conversion. Moreover, the enhanced process also reduces, through extraction, the amount of alkanol that is undesirably removed with the extract.

The present invention is described in further detail in connection with the following examples, it being understood that the same are for the purposes of illustration and not limitation.

EXAMPLE 1

A single stage transesterification of ethylene carbonate and methanol to form dimethyl carbonate and ethylene glycol was performed using potassium carbonate as a catalyst. The single stage experiment was conducted by combining a stream containing 57.83 weight percent of ethylene carbonate and 42.17 weight percent of methanol with the potassium carbonate catalyst in a glass reaction tube. The tube was equipped with a screw cap and O-ring seal and was designed to withstand the vapor pressures that develop at reaction conditions. The reaction conditions comprised a reaction temperature of 203° F., a reaction pressure of 80 psig, stoichiometric methanol, and an on stream time of 18 hours. The tubes were immersed in a constant temperature shaker bath to equilibrate. After equilibration, the tubes were cooled, opened, and the phases separated, weighed, and analyzed by gas chromatography. The results of the single stage transesterification of ethylene carbonate and methanol are presented in Table 1.

The single stage transesterification of ethylene carbonate with methanol resulted in an ethylene carbonate conversion of 45.0 percent, a methanol conversion of 26.8 percent, and a dimethyl carbonate yield of 36.1 percent. For purposes of determining alkylene carbonate conversion, methanol conversion, and dimethyl carbonate yield for Examples 1–6, the following calculation methods were employed:

$$\text{Ethylene Carbonate Conv.} = \frac{[\text{Wt Ethylene Carbonate in} - \text{Wt Ethylene Carbonate out}] \times 100}{[\text{Wt Ethylene Carbonate in}]}$$

$$\text{Methanol Conv.} = \frac{[\text{Wt Methanol in} - \text{Wt Methanol out}] \times 100}{[\text{Wt \% Methanol in}]}$$

$$\text{Dimethyl Carbonate Yield} = \frac{[\text{Wt Dimethyl Carbonate out}] \times 100}{[\text{Wt Ethylene Carbonate in}]}$$

EXAMPLE 2

A single stage transesterification of propylene carbonate and methanol to form dimethyl carbonate and propylene glycol was conducted in a manner similar to that set forth in Example 1. The single stage experiment was conducted by combining a stream containing 61.25 weight percent of propylene carbonate and 38.76 weight percent of methanol with the potassium carbonate catalyst in a glass reaction tube. The results of the single stage transesterification of propylene carbonate and methanol are presented in Table 1.

The single stage transesterification of propylene carbonate with methanol resulted in an propylene carbonate conversion of 29.2 percent, a methanol conversion of 22.2 percent, and a dimethyl carbonate yield of 20.7 percent, each substantially lower than those for ethylene carbonate.

EXAMPLE 3

A single stage transesterification and extraction experiment was conducted using a normal octane selective solvent to demonstrate the effectiveness of using reaction extraction for increasing ethylene carbonate transesterification reaction yields and conversions. The transesterification experiment was conducted using the feedstocks and experimental conditions set forth in Example 1. The normal octane was added at an 8:1 solvent to feed ratio by weight. The results of the single stage reaction extraction experiment for ethylene carbonate and methanol are presented in Table 1.

The single stage reaction extraction experiment for ethylene carbonate demonstrates that the addition of the extraction step increases ethylene carbonate conversion by over 43 percent to 64.4 percent, methanol conversion by over 69 percent to 45.5 percent, and dimethyl carbonate yield by over 39 percent to 50.3 percent. The use of reaction extraction results in a substantial improvement in all facets of ethylene carbonate transesterification. The extract product produced contains 99.29 weight percent dimethyl carbonate and normal octane which can be easily separated through distillation.

EXAMPLE 4

A single stage transesterification and extraction experiment using a normal octane selective solvent, was conducted in a manner similar to that set forth in Example 3, to demonstrate the effectiveness of reaction extraction for increasing propylene carbonate transesterification reaction yields and conversions. The results of the single stage reaction extraction experiment for propylene carbonate and methanol are presented in Table 1.

The single stage reaction extraction experiment demonstrates that the addition of the extraction step increases propylene carbonate conversion by over 51 percent to 44.1 percent, methanol conversion by over 55 percent to 34.9 percent, and dimethyl carbonate yield by over 36 percent to 28.2 percent. The use of reaction extraction results in a substantial improvement in all facets of propylene carbonate transesterification. The extract product produced contains 99.26 weight percent dimethyl carbonate and normal octane which can be easily separated through distillation.

TABLE 1

| Example | 1 | 2 | 3 | 4 |
|---|---|---|---|---|
| Process Conditions | | | | |
| Temperature, °F. | 203 | 203 | 203 | 203 |
| Pressure, psig | 80 | 80 | 80 | 80 |
| Time on Stream, hrs | 18.0 | 17.0 | 18.0 | 17.0 |
| Streams, g | | | | |
| Feed | 36.3 | 35.7 | 2.9 | 2.9 |
| Solvent | N/A | N/A | 22.8 | 22.7 |
| Raffinate | 35.6 | 35.1 | 2.0 | 2.3 |
| Extract | N/A | N/A | 23.3 | 22.7 |
| Wt. Bal., % | 98.1 | 98.3 | 98.4 | 97.7 |
| Raffinate Composition, Wt. % | | | | |
| Water | 0.12 | 0.09 | 0.28 | 0.14 |
| Methanol | 31.46 | 30.54 | 28.24 | 27.96 |
| Dimethyl Carbonate | 21.31 | 12.93 | 7.12 | 5.79 |
| Ethylene Glycol | 14.67 | N/A | 33.62 | N/A |
| Propylene Glycol | N/A | 12.32 | N/A | 21.98 |
| Ethylene Carbonate | 32.44 | N/A | 29.86 | N/A |
| Propylene Carbonate | N/A | 44.12 | N/A | 41.12 |
| Octane | N/A | 0.00 | 0.88 | 3.01 |
| Extract Composition, Wt. % | | | | |
| Water | N/A | N/A | 0.27 | 0.14 |
| Methanol | N/A | N/A | 0.44 | 0.39 |
| Dimethyl Carbonate | N/A | N/A | 3.01 | 1.62 |
| Ethylene Glycol | N/A | N/A | 0.00 | N/A |
| Propylene Glycol | N/A | N/A | N/A | 0.00 |
| Ethylene Carbonate | N/A | N/A | 0.00 | N/A |
| Propylene Carbonate | N/A | N/A | N/A | 0.21 |
| Octane | N/A | N/A | 96.28 | 97.64 |
| Methanol Conversion, % | 26.8 | 22.5 | 45.5 | 34.9 |
| Ethylene Carbonate Conversion, % | 45.0 | N/A | 64.4 | N/A |
| Propylene Carbonate Conversion, % | N/A | 29.2 | N/A | 44.1 |
| Dimethyl Carbonate Yield, % | 36.1 | 20.7 | 50.3 | 28.2 |

EXAMPLE 5

Figure 2:
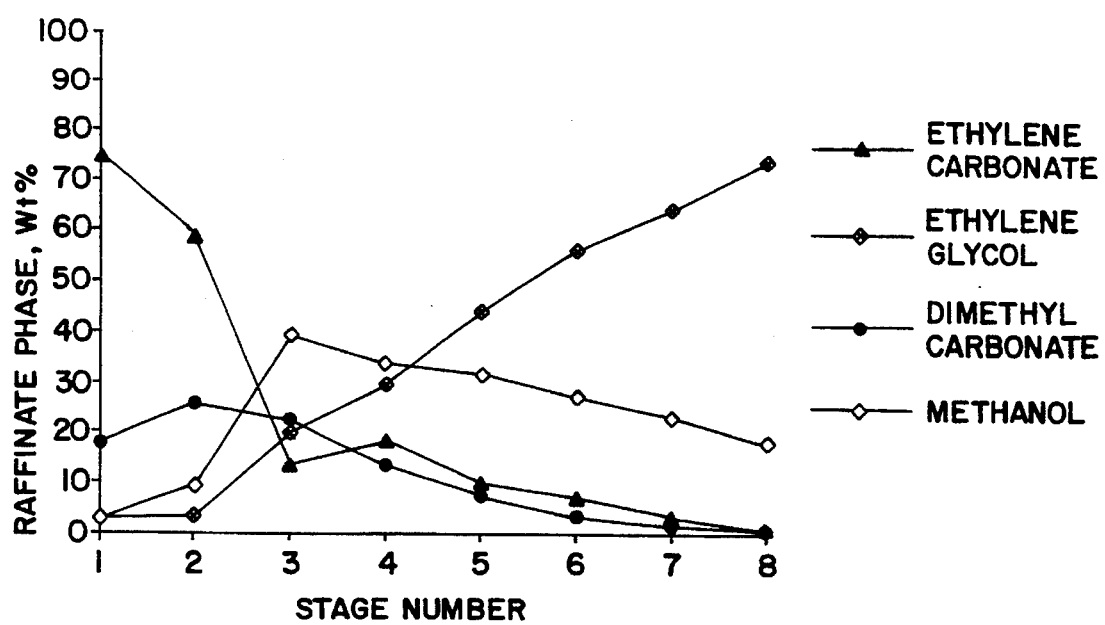
FIG. 2 is the concentration profile for both the extract and raffinate phases for a reaction extraction process utilizing two stages of rectification and six stages of stripping.
Figure 2:
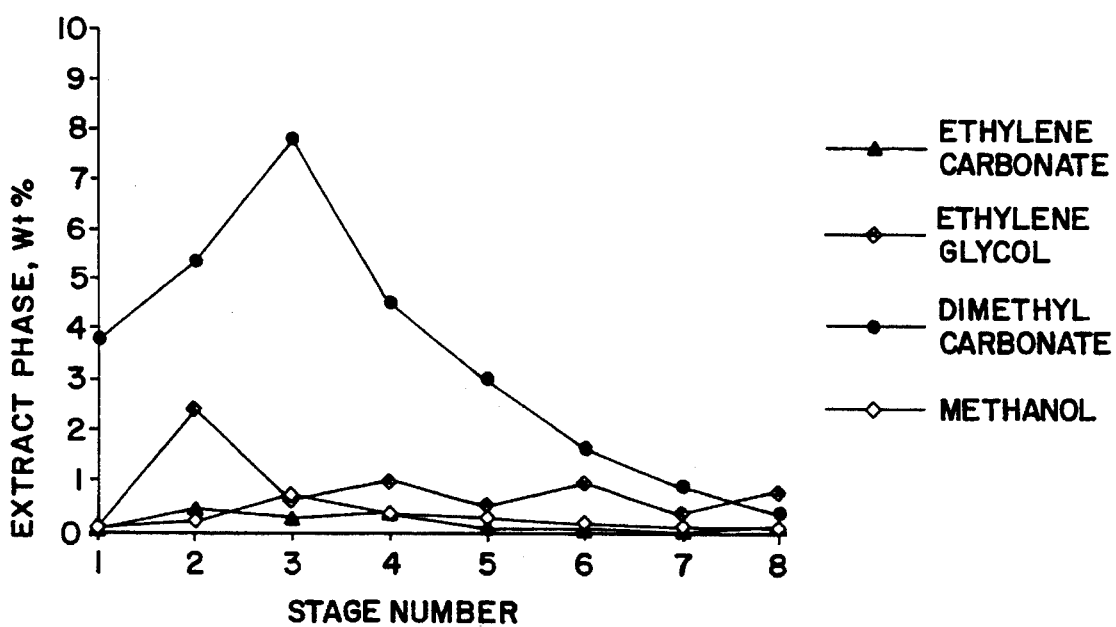

A multistage transesterification and extraction experiment, in accordance with the present invention, was conducted in a manner similar to that set forth in Example 3. In the multistage reaction extraction, the extract and raffinate phase were transferred from one tube to the next as needed. The multistage transesterification experiment was conducted to emulate a countercurrent multiple-contact liquid extraction where feed and solvent enter at opposite ends of the cascade with raffinate and extract solutions flowing countercurrently. The multistage transesterification and extraction was performed with 8 stages of reaction extraction and with each stage run as a batch experiment. Stages 1 and 2 functioned as catalyst-free rectifying stages. The potassium carbonate catalyst was dissolved in the methanol feed, entered the system at stage 3, and remained in the raffinate phase throughout the reaction extraction. The component distributions after equilibrium had been established for each stage of the multistage reaction extraction experiment for ethylene carbonate with methanol are presented in Table 2. The concentration profiles for each phase and at each stage are illustrated in FIG. 2.

TABLE 2

| Stage | Feed | 1 | 2 | 3 | 4 | 5 | 6 | 7 | 8 |
|---|---|---|---|---|---|---|---|---|---|
| Process Conditions | | | | | | | | | |
| Temperature, °F. | N/A | 194 | 194 | 194 | 194 | 194 | 194 | 194 | 194 |
| Pressure, psig | N/A | 80 | 80 | 80 | 80 | 80 | 80 | 80 | 80 |
| Time on Stream, hrs | N/A | 11.0 | 11.0 | 11.0 | 11.0 | 11.0 | 11.0 | 11.0 | 11.0 |

TABLE 2-continued

| Stage | Feed | 1 | 2 | 3 | 4 | 5 | 6 | 7 | 8 |
|---|---|---|---|---|---|---|---|---|---|
| Streams, g | | | | | | | | | |
| Feed | N/A | 3.0 | 2.8 | 2.8 | 2.9 | 3.1 | 3.0 | 2.9 | 2.9 |
| Solvent | N/A | 22.7 | 22.7 | 22.8 | 22.7 | 22.7 | 22.8 | 22.7 | 22.7 |
| Raffinate | N/A | 2.8 | 2.8 | 3.1 | 3.1 | 2.1 | 2.5 | 1.6 | 1.5 |
| Extract | N/A | 19.3 | 23.8 | 20.2 | 23.8 | 19.4 | 23.0 | 18.5 | 23.1 |
| Wt. Bal., % | N/A | 85.2 | 104.3 | 91.0 | 105.1 | 83.3 | 98.8 | 78.5 | 96.1 |
| Raffinate Composition, Wt. % | | | | | | | | | |
| Water | 0.00 | 0.18 | 0.15 | 0.21 | 0.22 | 0.25 | 0.40 | 0.42 | 0.55 |
| Methanol | 42.17 | 2.91 | 9.29 | 39.13 | 33.71 | 31.49 | 27.21 | 23.03 | 18.16 |
| Dimethyl Carbonate | 0.00 | 17.87 | 25.68 | 22.34 | 13.57 | 7.20 | 3.29 | 1.60 | 0.52 |
| Ethylene Glycol | 0.00 | 2.81 | 3.37 | 20.01 | 29.45 | 44.10 | 56.09 | 64.23 | 73.75 |
| Ethylene Carbonate | 57.83 | 74.80 | 59.24 | 13.76 | 18.51 | 10.04 | 7.21 | 3.35 | 0.95 |
| Diethylene Glycol | 0.00 | 0.83 | 0.91 | 2.04 | 2.73 | 4.54 | 5.18 | 5.88 | 4.51 |
| Octane | 0.00 | 0.60 | 1.36 | 2.51 | 1.81 | 2.36 | 0.62 | 1.49 | 1.56 |
| Extract Composition, Wt. % | | | | | | | | | |
| Water | N/A | 0.20 | 0.10 | 0.11 | 0.08 | 0.11 | 0.10 | 0.10 | 0.09 |
| Methanol | N/A | 0.09 | 0.20 | 0.74 | 0.35 | 0.28 | 0.19 | 0.14 | 0.10 |
| Dimethyl Carbonate | N/A | 3.80 | 5.38 | 7.83 | 4.55 | 3.05 | 1.69 | 0.94 | 0.40 |
| Ethlyene Glycol | N/A | 0.06 | 2.42 | 0.64 | 1.03 | 0.55 | 1.00 | 0.41 | 0.85 |
| Ethylene Carbonate | N/A | 0.05 | 0.46 | 0.29 | 0.40 | 0.09 | 0.07 | 0.05 | 0.12 |
| Diethylene Glycol | N/A | 0.13 | 1.22 | 0.11 | 0.37 | 0.08 | 0.28 | 0.06 | 0.22 |
| Octane | N/A | 95.67 | 90.22 | 90.26 | 93.22 | 95.84 | 96.67 | 98.30 | 98.22 |
| Methanol Conversion, % | 76.3 | | | | | | | | |
| Ethylene Carbonate Conversion, % | 98.7 | | | | | | | | |
| Dimethyl Carbonate Yield, % | 44.2 | | | | | | | | |

Table 2 and FIG. 2 clearly illustrate that the concentration of ethylene carbonate in the raffinate phase decreases significantly in stage 3, where it is combined with methanol and catalyst, and then more gradually in stages 4 through 8 until it is reduced to less than 1 weight percent. The ethylene glycol concentration in the raffinate phase increases almost linearly across stages 1 through 8 and more particularly, stages 2 through 8. The final ethylene glycol concentration at stage 8 is 73.75 weight percent. Analysis of the extract phase shows that the dimethyl carbonate concentration increases at an increasing rate from stages 8 through 2 to where it is maximized at stage 2 at a level of 7.83 weight percent. Dimethyl carbonate concentration actually decreases across rectifying stages 1 and 2 to a level of 3.80 weight percent. This indicates that rectifying stages 1 and 2 are actually back extracting portions of the dimethyl carbonate from the normal octane solvent and that it may be desirable to reduce the number of rectifying stages.

EXAMPLE 6

Figure 3:
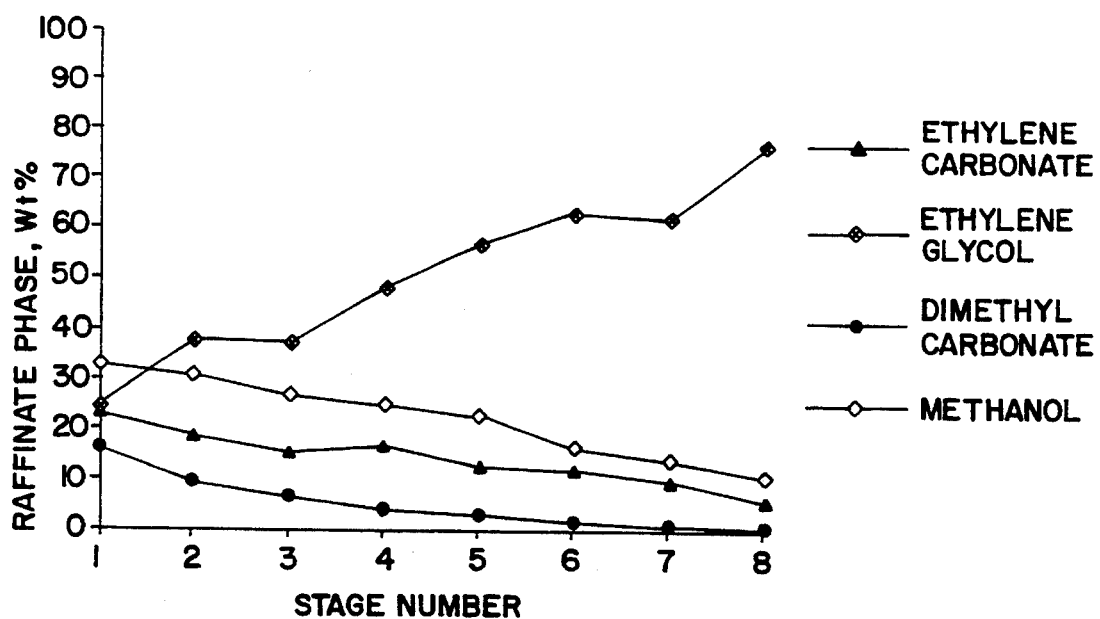
FIG. 3 is the concentration profile for both the extract and raffinate phases for a reaction extraction process utilizing zero stages of rectification and eight stages of stripping.
Figure 3:
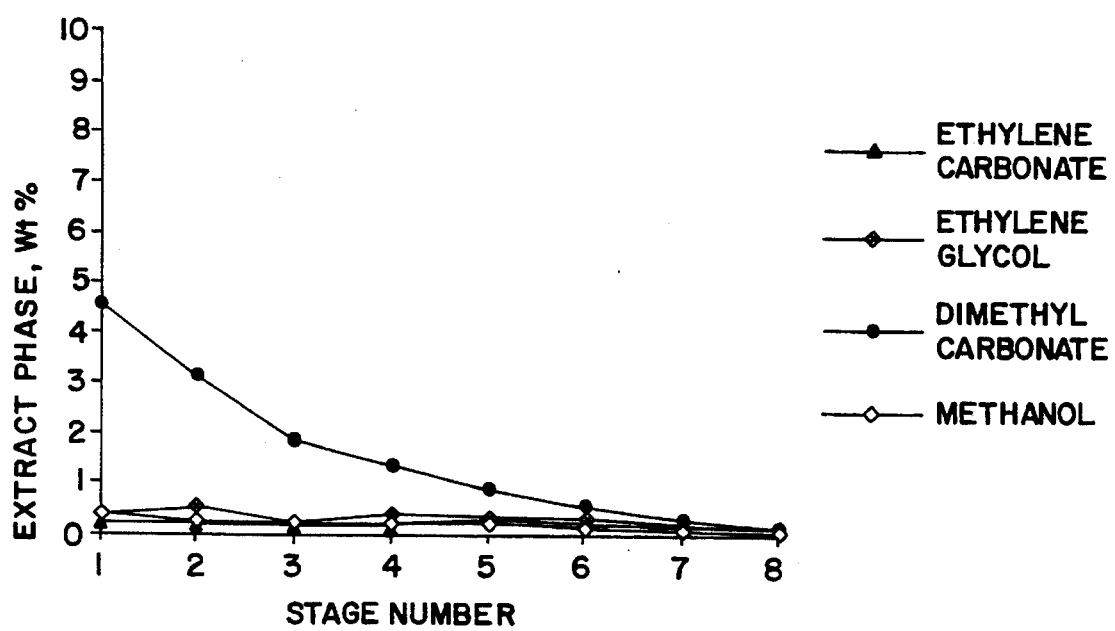

A multistage transesterification and extraction experiment, in accordance with the present invention, was conducted in a manner similar to that set forth in Example 5. However, Example 6 was conducted without any rectifying stages and with the methanol, ethylene carbonate, and potassium carbonate catalyst all added to the system at stage 1. In addition, the equilibrium time for each stage was reduced from 11.0 hours to 0.5 hours. The component distributions after equilibrium had been established for each stage of the multistage reaction extraction experiment for ethylene carbonate and methanol are presented in Table 3. The concentration profiles for each phase and at each stage are illustrated in FIG. 3.

TABLE 3

| Stage | Feed | 1 | 2 | 3 | 4 | 5 | 6 | 7 | 8 |
|---|---|---|---|---|---|---|---|---|---|
| Process Conditions | | | | | | | | | |
| Temperature, °F. | N/A | 194 | 194 | 194 | 194 | 194 | 194 | 194 | 194 |
| Pressure, psig | N/A | 80 | 80 | 80 | 80 | 80 | 80 | 80 | 80 |
| Time on Stream, hrs | N/A | 0.50 | 0.50 | 0.50 | 0.50 | 0.50 | 0.50 | 0.50 | 0.50 |
| Streams, g | | | | | | | | | |
| Feed | N/A | 3.0 | 2.8 | 2.8 | 2.9 | 3.1 | 3.0 | 2.9 | 2.9 |
| Solvent | N/A | 22.7 | 22.7 | 22.8 | 22.7 | 22.7 | 22.8 | 22.7 | 22.7 |
| Raffinate | N/A | 2.8 | 2.2 | 1.7 | 1.5 | 1.2 | 2.0 | 1.5 | 1.6 |
| Extract | N/A | 21.7 | 22.7 | 22.4 | 21.5 | 22.5 | 21.6 | 22.7 |  |
| Wt. Bal., % | NIA | 95.3 | 97.6 | 89.8 | 93.4 | 88.0 | 95.0 | 90.2 | 94.9 |
| Raffinate Composition, Wt. % | | | | | | | | | |
| Water | 0.00 | 0.97 | 0.38 | 0.60 | 0.34 | 0.64 | 0.35 | 0.56 | 0.40 |
| Methanol | 42.17 | 32.64 | 30.39 | 26.57 | 24.69 | 22.43 | 16.22 | 13.61 | 10.29 |

TABLE 3-continued

| Stage | Feed | 1 | 2 | 3 | 4 | 5 | 6 | 7 | 8 |
|---|---|---|---|---|---|---|---|---|---|
| Dimethyl Carbonate | 0.00 | 15.85 | 8.95 | 6.30 | 3.69 | 2.70 | 1.32 | 0.80 | 0.34 |
| Ethylene Glycol | 0.00 | 24.07 | 37.61 | 37.07 | 48.55 | 57.15 | 63.69 | 62.30 | 76.91 |
| Ethylene Carbonate | 57.83 | 23.08 | 18.39 | 16.10 | 16.71 | 12.37 | 11.85 | 9.62 | 5.58 |
| Diethylene Glycol | 0.00 | 1.60 | 3.34 | 2.44 | 4.71 | 3.95 | 6.04 | 4.20 | 5.81 |
| Octane | 0.00 | 1.79 | 0.93 | 11.92 | 1.31 | 0.76 | 0.53 | 8.91 | 0.67 |
| Extract Composition, Wt. % | | | | | | | | | |
| Water | N/A | 0.15 | 0.12 | 0.15 | 0.10 | 0.16 | 0.11 | 0.16 | 0.10 |
| Methanol | N/A | 0.36 | 0.24 | 0.ig | 0.19 | 0.21 | 0.15 | 0.11 | 0.07 |
| Dimethyl Carbonate | N/A | 4.53 | 3.15 | 1.86 | 1.39 | 0.92 | 0.59 | 0.32 | 0.17 |
| Ethlyene Glycol | N/A | 0.35 | 0.52 | 0.23 | 0.39 | 0.37 | 0.34 | 0.20 | 0.23 |
| Ethylene Carbonate | N/A | 0.21 | 0.19 | 0.17 | 0.20 | 0.27 | 0.21 | 0.19 | 0.16 |
| Diethylene Glycol | N/A | 0.00 | 0.14 | 0,00 | 0.00 | 0.00 | 0.00 | 0.00 | 0.00 |
| Octane | N/A | 94.38 | 95.64 | 97.40 | 97.73 | 98.07 | 98.60 | 99.02 | 99.27 |
| Methanol Conversion, % | 80.1 | | | | | | | | |
| Ethylene Carbonate Conversion, % | 92.2 | | | | | | | | |
| Dimethyl Carbonate Yield, % | 58.9 | | | | | | | | |

FIG. 3 provides indications that the reduction in equilibrium time of from 11.0 hours to 0.5 hours for each stage resulted in less dimethyl carbonate extraction per stage. However, the concentration of dimethyl carbonate in the extract phase continued to increase from stage 8 to stage 1 where it reached its maximum concentration at 4.53 weight percent. The final dimethyl carbonate concentration exceeded that for the rectifying experiment of Example 5 (i.e., 3.80 weight percent), but did not exceed the stage 3 dimethyl carbonate loading for the rectifying experiment of 7.83 weight percent. This indicates that additional reaction extraction stages or increased equilibrium time could provide increased concentrations of dimethyl carbonate in the final extract product. The concentration of ethylene glycol in the raffinate phase again increased across stages 1 through 8 where it reached a final level of 76.9 weight percent, slightly higher than for the rectifying experiment of Example 5 (i.e., 73.7 weight percent).

In the experiments conducted in both of Examples 5 and 6, diethylene glycol was identified as a side-product through the use of Gas Chromatography—Infrared Spectroscopy. Diethylene glycol is generally produced from the base catalyzed reaction of two moles of ethylene glycol to form one mole of diethylene glycol and one mole of water. It is theorized that the formation of water hydrolyzed some of the dimethyl carbonate into methanol and carbon dioxide as indicated by the dimethyl carbonate/ethylene glycol mole ratio of significantly less than 1.0 (i.e., 0.54 for Example 5 and 0.52 for Example 6). In the absence of side reactions, the dimethyl carbonate/ethylene glycol molar ratio would be anticipated to be about 1.0.

A comparison of the conversion and yield data for the single-stage and multi-stage reaction extraction experiments of Examples 3, 5, and 6 reveals that a significantly higher per pass conversion of ethylene carbonate and methanol is achieved with the multi-stage processes of Examples 5 and 6 compared to the single-stage process of Example 3. Multi-Stage reaction extraction improved ethylene carbonate conversion by an average of 48.1 percent, to 95.4 percent and methanol conversion by an average of over 71.8 percent, to 78.2 percent. With regard to dimethyl carbonate yield however, dimethyl carbonate yield changed adversely by −12.3 percent, to 44.2 weight percent in Example 5 and favorably by 17.1 percent, to 58.9 weight percent in Example 6. The disparate results are largely attributed to the difference in equilibrium time per stage between Example 5 (11.0 hours) and Example 6 (0.5 hours) where increased amounts of the dimethyl carbonate may have decomposed to methanol and carbon dioxide as previously described.

Examples 1 through 6 clearly illustrate that multi-stage reaction extraction can be used to drive the ethylene carbonate and methanol feedstocks to near complete conversion. Optimization of the molar feed ratio, total number and type of stages, stage residence time, and reaction temperature and pressure can lead to even further improvements in performance.

Other embodiments of the invention will be apparent to those skilled in the art from a consideration of this specification or from practice of the invention disclosed herein. It is intended that this specification be considered as exemplary only with the true scope and spirit of the invention being indicated by the following claims.

That which is claimed is:

1. An extraction reaction process for reacting feedstocks comprising alkylene carbonate and alkanol to form reaction products comprising alkyl carbonate, comprising the steps of:

reacting said feedstocks comprising alkylene carbonate and alkanol in a reaction zone at reaction conditions for producing said reaction products comprising alkyl carbonate; and substantially concurrently with said reacting step and within said reaction zone, contacting said feedstocks comprising alkylene carbonate and alkanol and said reaction products comprising alkyl carbonate with a selective solvent, selective for extracting alkyl carbonate from said reaction zone;

wherein said selective solvent comprises a distribution coefficient with respect to said alkyl carbonate that is substantially different than the distribution coefficient of the selective solvent with respect to said alkanol.

2. The process of claim 1 wherein said selective solvent forms a first mixture comprising alkyl carbonate thereby defining a second mixture comprising at least one member selected from the group consisting of alkylene glycol, alkylene carbonate, and alkanol and said first and second mixtures have substantially different specific gravities.

3. The process of claim 1 wherein said selective solvent has an aromatics concentration of more than 1 percent by weight and an olefin concentration ranging from 0 to 40 percent by weight.

4. The process of claim 1 wherein said reaction conditions comprise a catalyst and said catalyst comprises at least one component selected from the group consisting of the alkali metal carbonates, the alkali metal hydroxides, and the sulfated polystyrene resins.

5. The process of claim 4 wherein said catalyst is a solid particulate catalyst and said reaction zone comprises a fixed bed of said solid particulate catalyst.

6. The process of claim 4 wherein said catalyst is soluble in said alkanol, and said catalyst is directed to said reaction zone in solution with said alkanol.

7. The process of claim 4 wherein said catalyst is soluble in said alkylene carbonate, and said catalyst is directed to said reaction zone in solution with said alkylene carbonate.

8. The process of claim 1 wherein said reaction zone comprises a top section and a bottom section, at least one of said feedstocks comprising alkylene carbonate and alkanol is directed to the top section of said reaction zone, at least a portion of said selective solvent is directed to the bottom section of said reaction zone, and at least a portion of said selective solvent countercurrently extracts at least a portion of at least one of said reaction products comprising alkyl carbonate for removal from said reaction zone.

9. The process of claim 8 wherein water is added to said bottom section of said reaction zone.

10. The process of claim 1 wherein said alkylene carbonate is ethylene carbonate, said alkanol is methanol, said alkyl carbonate is dimethyl carbonate, said reaction products also comprise ethylene glycol and said catalyst is potassium carbonate.

11. The process of claim 2 wherein at least a portion of said first mixture comprising said selective solvent and said extracted alkyl carbonate is removed from said reaction zone and directed to a separation device for separating at least a portion of said selective solvent from said extracted alkyl carbonate and wherein at least a portion of said separated selective solvent is recycled back to said reaction zone.

12. An extraction reaction process for reacting feedstocks comprising alkylene carbonate and alkanol to form reaction products comprising alkyl carbonate and alkylene glycol at a yield in excess of the equilibrium yield of such reaction products with respect to such feedstocks, comprising the steps of:

reacting said feedstocks comprising alkylene carbonate and alkanol in a reaction vessel at reaction conditions in the presence of a catalyst for producing said reaction products comprising alkyl carbonate and alkylene glycol; and substantially concurrently with said reacting step and within said reaction vessel, contacting said feedstocks comprising alkylene carbonate and alkanol and said reaction products comprising alkyl carbonate and alkylene glycol with a hydrocarbon solvent, selective for extracting alkyl carbonate from said reaction zone thereby increasing the yield of said reaction products comprising alkyl carbonate and alkylene glycol with respect to said feedstocks comprising alkylene carbonate and alkanol to in excess of their equilibrium yield;

wherein said hydrocarbon solvent comprises a distribution coefficient with respect to said alkyl carbonate that is substantially different than the distribution coefficient of the hydrocarbon solvent with respect to said alkanol; and wherein said hydrocarbon solvent forms a first mixture comprising a substantial portion of alkyl carbonate thereby defining a second mixture comprising at least one member selected from the group consisting of alkylene glycol, alkylene carbonate, and alkanol and said first and second mixtures have substantially different specific gravities.

13. The process of claim 12 wherein said hydrocarbon solvent comprises at least one component selected from the group consisting of light virgin naphtha, catalytic cracking naphtha, catalytic reformate, and aromatic derivatives of catalytic reformate.

14. The process of claim 12 wherein said catalyst comprises potassium carbonate.

15. The process of claim 14 wherein said catalyst is a solid particulate catalyst and said reaction zone comprises a fixed bed of said solid particulate catalyst.

16. The process of claim 14 wherein said catalyst is soluble in at least one component selected from the group consisting of said alkanol and said alkylene carbonate and said catalyst is directed to said reaction zone in solution with one or both of said alkanol and said alkylene carbonate.

17. The process of claim 12 wherein said alkylene carbonate is ethylene carbonate, said alkanol is methanol, said alkyl carbonate is dimethyl carbonate, said alkylene glycol is ethylene glycol, and said catalyst is potassium carbonate.

18. The process of claim 12 wherein said first mixture comprising said hydrocarbon solvent and said extracted alkyl carbonate is removed from said reaction vessel and directed to a separation device for separating at least a portion of said hydrocarbon solvent from said extracted alkyl carbonate and wherein at least a portion of said separated hydrocarbon solvent is recycled back to said reaction vessel.

19. The process of claim 12 wherein said second mixture comprising at least one member selected from the group consisting of alkylene glycol, alkylene carbonate, and alkanol and water is directed to a hydrolysis zone for producing a product stream comprising alkylene glycol and carbon dioxide.

20. The process of claim 12 wherein water is added to said reaction vessel.

* * * * *

UNITED STATES PATENT AND TRADEMARK OFFICE
CERTIFICATE OF CORRECTION

PATENT NO. : 5,489,703
DATED : February 6, 1996
INVENTOR(S) : Pacheco et al.

It is certified that error appears in the above-indentified patent and that said Letters Patent is hereby corrected as shown below:

| Col. | Line | |
|---|---|---|
| 8 | 26-27 | "The reaction can generally be carded out at any convenient temperature" should read --The reaction can generally be carried out at any convenient temperature-- |
| 19 | 53 | in "TABLE 1" in the row labelled "1" patent reads "NIA" patent should read --N/A-- |
| 20 | 66 | in "TABLE 2" in the row labelled "3" patent reads "so" patent should read --80-- |
| 21 | 7 | in "TABLE 2-continued" in the row labelled "1" patent reads "2.8" patent should read --2.6-- |
| 22 | 16 | in "TABLE 2-continued" in the row labelled "5" patent reads "2.36" patent should read --2.38-- |
| 23 | 5 | in "TABLE 3-continued" in the row labelled "3" patent reads "16.10" patent should read --15.10-- |

UNITED STATES PATENT AND TRADEMARK OFFICE
CERTIFICATE OF CORRECTION

PATENT NO. : 5,489,703
DATED : February 6, 1996
INVENTOR(S) : Pacheco et al.

It is certified that error appears in the above-indentified patent and that said Letters Patent is hereby corrected as shown below:

| Col. | Line | |
|---|---|---|
| 23 | 7 | in "TABLE 3-continued" in the row labelled "3" patent reads "11,92" patent should read --11.92-- |
| 23 | 11 | in "TABLE 3-continued" in the row labelled "3" patent reads "O.ig" patent should read --0.19-- |
| 23 | 15 | in "TABLE 3-continued" in the row labelled "3" patent reads "0,00" patent should read --0.00-- |

Signed and Sealed this

Sixteenth Day of July, 1996

BRUCE LEHMAN

Attest:

Attesting Officer

Commissioner of Patents and Trademarks